United States Patent [19]

Köhler et al.

[11] 4,330,679

[45] May 18, 1982

[54] PROCESS FOR THE PREPARATION OF ALKYL TERT.-ALKYL ETHERS

[75] Inventors: Hans-Dieter Köhler; Bernhard Schleppinghoff, both of Dormagen, Fed. Rep. of Germany

[73] Assignee: EC Erdölchemie GmbH, Cologne, Fed. Rep. of Germany

[21] Appl. No.: 276,761

[22] Filed: Jun. 24, 1981

[30] Foreign Application Priority Data

Jul. 12, 1980 [DE] Fed. Rep. of Germany ....... 3026504

[51] Int. Cl.³ .............................................. C07C 41/06
[52] U.S. Cl. ................................ 568/697; 252/429 A; 252/430; 260/429 BQ
[58] Field of Search .......................................... 568/697

[56] References Cited

U.S. PATENT DOCUMENTS 3,718,701  2/1973  Holovka et al. ................... 568/697

FOREIGN PATENT DOCUMENTS 906453   3/1954  Fed. Rep. of Germany ...... 568/697
1800380  8/1969  Fed. Rep. of Germany .
2629769  5/1978  Fed. Rep. of Germany .
1583594  10/1969 France .
49-4661109 6/1974 Japan ................................. 568/697

Primary Examiner—Howard T. Mars
Attorney, Agent, or Firm—Sprung, Horn, Kramer & Woods

[57] ABSTRACT

In a process for the preparation of an alkyl tert.-alkyl ether by reaction of an isoolefin branched at the double bond and an alkanol in the presence of a cation exchanger, the improvement which comprises:

(a) Employing as the cation exchanger a macroporous or gelatinous acid cation exchanger in the $H^+$ form which has been charged with 0.1 to 5 grams, per one liter of dry cation exchanger, of an elementary form of a metal of sub-groups VI, VII or VIII of the periodic table of elements (Mendeleev) which cation exchanger is crosslinked with the degree of crosslinking of 2 to 65% and has a specific surface area of 5 to 750 square meters per gram on the basis of dry cation exchange resin; and (b) The reaction is carried out in the liquid phase at a temperature of 30° to 140° C. at a pressure of 2 to 100 bars employing a molar ratio of isoolefin to alkanol of 0.1 to 5.

14 Claims, No Drawings

PROCESS FOR THE PREPARATION OF ALKYL TERT.-ALKYL ETHERS

The present invention relates to a process for the preparation of alkyl tert.-alkyl ethers from isoolefins branched at the double bond and alkanols in the presence of cation exchangers which are charged with the elementary form of a metal sub-group VI, VII or VIII of the periodic table.

It is known that methyl tert.-butyl ether is an antiknock additive for fuel for carburettor-type engines, and additonally reduces, to a certain extent, the concentration of carbon monoxide in the exhaust of a combustion engine (German Offenlegungsschrift No. 2,419,439). It is already known that olefins, optionally as mixtures with paraffin hydrocarbons, can be reacted with primary or secondary alcohols in the presence of acid catalysts to give alkyl ethers. Acid catalysts which are used are, for example, inorganic acids, such as sulphuric acid, or organic acids, such as p-toluenesulphonic acids, or acid cation exchangers which contain sulphonic acid groups and are based on crosslinked vinyl-aromatic polymers (German Auslegeschrift No. 1,224,294). The reaction between an olefin and an alcohol to give the corresponding ether has an equilibrium point which is more favourable for synthesis of the ether the lower the reaction temperature, but at the same time the rate of reaction decreases (German Offenlegungsschrift No. 2,521,964). In order to improve the rate of conversion under otherwise unchanged reaction conditions, it has been proposed to recycle part of the reaction mixture of the olefin and a primary alcohol directly into the feed material for the preparation reactor (German Offenlegungsschrift No. 2,911,077). A higher conversion of olefin, for better utilization of this raw material, can also be achieved by using an excess of alcohol, separating off the excess alcohol at a later date by extraction with water (German Offenlegungsschrift No. 2,419,439) or by extractive distillation with polar solvents (Japanese Patent Application No. 7300509) requiring considerable additional expenditure. Processes in which recycling of the unreacted olefins in direct or indirect form, such as after passing through physical separation operations, is envisaged in order to increase the conversion of olefine indeed increase the yield of the olefins employed, but necessitate a higher expenditure on capital costs and energy costs for larger reaction vessels and the separation devices required.

It is furthermore known that the reaction of methanol and isobutylene to give methyl tert.-butyl ether can be catalyzed with ruthenium trichloride (U.S. Pat. No. 3,718,701).

It is also known that olefins can be converted into dimeric and trimeric oligomers and higher oligomers in the presence of acid cation exchangers (Erdöl and Kohle 19, 497 (1966)).

A process has now been found for the preparation of alkyl tert.-alkyl ethers from isoolefins branched at the double bond and alkanols in the presence of cation exchangers, which is characterized in that macroporous or gelatinous acid cation exchangers in the $H^+$ form which have been charged with 0.1 to 5 g, per 1 liter of dry cation exchanger, of the elementary form of a metal of sub-groups VI, VII or VIII of the periodic table of the elements (Mendeleev) and which have degrees of crosslinking of 2 to 65% and a specific surface area of 5 to 750 m$^2$ per g of dry exchanger resin are used for the etherification, and the reaction is carried out in the liquid phase at 30° to 140° C., under a pressure of 2 to 100 bars and with a molar ratio of isoolefin to alkanol of 0.1 to 5, if desired in the presence of a solvent.

Macroporous or gelatinous, acid cation exchangers which are prepared, for example, by copolymerization of vinyl monomers with divinyl crosslinking agents in the presence of solvents which dissolve the monomers but exhibit no swelling effect on the polymers formed (German Auslegeschrift No. 1,113,570 and U.S. Pat. No. 3,586,646) are employed for the process according to the invention. Vinyl monomers which may be mentioned are, inter alia, styrene and acrylates. A useful divinyl crosslinking agent is, for example, divinylbenzene. The degree of crosslinking depends on the amount of the divinyl crosslinking agent and can vary, for example from 2 to 65%, preferably from 8 to 25%, these figures given denoting the amount of cross-linking agent, relative to the total amount of comonomers.

Examples of acid groups are carboxyl groups, which are obtained by saponification of acrylate, or sulphonic acid groups, which can be introduced by subsequent sulphonation.

Strongly acid styrene/divinylbenzene polymers which contain sulphonic acid groups are preferably employed for the process according to the invention. Such cation exchangers are commercially available, for example under the name LEWATIT SPC 118, LEWATIT SPC 120, Amberlite 200 C, Dowex MSC-1 or Duolite C 26.

The cation exchangers which can be employed according to the invention have a specific surface area of, for example, 5 to 750 m$^2$ per g, preferably 50 to 250 m$^2$ per g. The mean pore radius can vary within the range from 50 to 1,200 Å, preferably from 70 to 500 Å. If the cation exchangers are employed in the form of bead polymers, particle sizes of, for example, 0.1 to 2 mm are used. If the cation exchangers are employed in the form of pulverulent resins, particle distributions of, for example, 10 to 100$\mu$ can be used.

Such cation exchangers in the $H^+$ form which have been charged with 0.1 to 5 g, preferably 0.2 to 3 g, per liter of dry cation exchanger, of the elementary form of a metal of sub-groups VI, VII or VIII of the periodic table of the elements are used in the process according to the invention. Examples which may be mentioned of metals of sub-groups VI, VII or VIII of the periodic table of the elements (Mendeleev) are: chromium, molybdenum, tungsten, manganese, technetium, rhenium, iron, cobalt, nickel, ruthenium, rhodium, palladium, osmium, iridium and platinum, preferably chromium, rhenium, palladium, platinum or iron.

In order to charge the cation exchanger with the metals mentioned, the desired metal, in the form of a non-complex, cationic salt, is brought together with the cation exchanger in the $H^+$ form batchwise in a manner which is in itself known. Examples of such salts which may be mentioned are the chlorides, bromides, nitrates, sulphates and acetates. The amount of salt to be employed is chosen such that the elementary metal is present in an amount of 0.1 to 5 g, preferably 0.2 to 3 g, per liter of exchanger, and can be determined by the expert by simple testing. It may be advantageous for the acid formed during reaction of the cation exchanger with the metal salt to be neutralized. This neutralization can be carried out during or after the reaction of the cation exchanger with the salt. An alkaline compound, if appropriate in the form of its aqueous solution, such as sodium hydroxide, potassium hydroxide, ammonium hydroxide, sodium carbonate, potassium carbonate or ammonium carbonate, can be used for this neutralization. After reaction with the metal salt, the cation exchanger is washed until the runnings are neutral, and is then dried at elevated temperature, if necessary under reduced pressure. Drying at 100° C. for 24 hours under a waterpump vacuum may be mentioned by way of example.

In order to convert the ions of a metal of subgroups VI, VII or VIII of the periodic table (Mendeleev) which are fixed on the cation exchanger into the elementary form, the cation exchanger which has been charged with the metal ions and dried is treated in a hydrogen atmosphere under a pressure of 2 to 50 bars, preferably 20 to 30 bars, and at a temperature of 50 to 140° C., preferably 80° to 120° C.

The reaction, according to the invention, of the branched isoolefins with the alkanols in the presence of the cation exchanger which has been charged with the elementary metals can be carried out in the liquid or gaseous phase, preferably in the liquid phase. A temperature of 30° to 140° C., preferably 50° to 130° C., particularly preferably 70° to 120° C. and very particularly preferably 75° to 110° C., may be mentioned as an example of the temperature for this reaction. The reaction is carried out under a pressure of 2 to 100 bars, preferably 3 to 30 bars. Pressure is at least 5, especially at least and more especially at least 10 bares are particularly contemplated e.g. 10 to 30 bars. In the case where the process is to be carried out in the preferred manner in the liquid phase, those combinations of temperature and pressure, within the scope of the temperatures and pressures mentioned, with which at least some of the reaction product is present in the liquid phase are always chosen.

Isoolefins which are branched at the double bond are employed in the process according to the invention. Such isolofins with 4 to 12 carbon atoms, preferably 4 to 8 carbon atoms and particularly preferably 4 to 6 carbon atoms, hydro-carbons, such as isobutylene, methylbutenes, methylpentenes, dimethylpentenes, methylhexenes and dimethylhexenes, may be mentioned as examples.

Such olefins can be employed in a pure form or in the form of a mixture of such an olefin and saturated hydrocarbons. For example, a fraction which is obtained from cracking processes in a refinery and which contains one of the abovementioned isoolefins which is branched at the double bond, in addition to saturated hydrocarbons and, in some cases, inert gases, such as nitrogen, hydrogen or carbon dioxide, can be employed. It is furthermore possible for mixtures or cracked fractions which contain 2 or more isoolefins which are branched at the double bond, optionally in addition to paraffins and/or the inert substances mentioned, to be employed in the process according to the invention and for the alkyl tert.-alkyl ethers obtained after carrying out the reaction according to the invention to be separated by suitable measures, for example by distillation.

Examples which may be mentioned of alkanols which can be employed in the process according to the invention are those with 1 to 8, preferably 1 to 6 and particularly preferably 1 to 4, carbon atoms, such as methanol, ethanol, propanol, butanols, hexanols or octanols.

The isoolefin which is branched at the double bond is employed in a molar ratio to the alkanol of 0.1 to 5, preferably 0.5 to 2 and particularly preferably 0.9 to 1.1.

The process according to the invention can be carried out either continuously or discontinuously.

In the discontinuous variant, the process can be carried out, for example, as follows:

The isoolefin to be etherified, if appropriate as a mixture with one or more other isoolefins and/or inert hydrocarbons, is mixed in a closed reactor with approximately the molar amount, relative to the isoolefins of methanol, and with the exchanger resin described above, in a ratio of 10 parts by weight of reaction mixture per part by weight of exchanger resin, and the mixture is stirred or shaken under pressure at elevated temperature for about half an hour to 5 hours until the etherification has ended. The reaction mixture can then be let down and decanted off from the exchanger resin. The reaction vessel is thus charged with a new reaction batch 15 times, reusing the exchanger resin, without a noticeable decrease in the activity of the catalyst being observed.

In the continuous process variant, the procedure can be, for example, as follows:

A stainless steel vessel or glass vessel which can be heated, for example 1 or more reaction tubes which can be heated, is filled with the cation exchanger described above. The isoolefin, or one of its mixtures described above, and the alkanol, individually or as a mixture, are passed through the exchanger bed, which can be heated externally, from the bottom upwards or vice versa, for example in the trickle phase. This operation is preferably carried out with a constant flow rate. The most advantageous conditions for the various isoolefins or their mixtures can be found by simple testing, that is to say by varying the pressure, the temperature and the throughput over the catalyst or the residence time. The material flowing out of the reactor is collected and the content of ether therein is determined, for example by analysis by gas chromatography. The throughput over the catalyst A is defined as the ratio of the amount of hydrocarbon mixture in ml to the amount of ion exchanger catalyst in ml per time in hours. In the process according to the invention, throughputs over the catalyst of A=0.1 to A=10 can be established.

It is possible for some of the reaction mixture to be recycled directly from the reactor, the weight ratio of the recycled stream to the discharge stream being 0.1 to 10:1, preferably 1:1 to 2:1.

The process according to the invention is distinguished by the fact that isoolefins and alkanols can be reacted almost quantitatively to give the corresponding ether in one reactor throughput at industrially useful space velocities.

It is surprising that the etherification according to the invention can be carried out at relatively high temperatures and thus with relatively high space/time yields without noticeable oligomerization of the olefin proceeding, such as, according to the state of the art, was to be expected in the presence of acid cation exchangers.

EXAMPLES

The expression throughput over the catalyst a used in the examples is defined by the following quotient:

$$A = \frac{\text{amount of hydrocarbon mixture (ml)}}{\text{amount of catalyst (ml} \cdot \text{time (hours)}}$$

EXAMPLE 1

A macroporous cation exchanger is prepared according to German Patent Specification No. 1,113,570 Example 3, the disclosure of which is hereby incorporated herein by reference. An amount of palladium acetate is made available batchwise to the water-moist H+ form of this cation exchanger such that, after reduction of hydrogen, 0.75 g of Pd/liter of dry resin are present on the cation exchanger. The acid liberated during the treatment with palladium acetate is neutralized with 1% strength by weight NaOH. The cation exchanger, which has been washed until the runnings are neutral, is then dried at 100° C. under a waterpump vacuum for 24 hours.

The palladium on the cation exchanger is activated at between 90° and 100° C. and under 20 to 25 bars of $H_2$ in the course of 48 hours.

EXAMPLE 2

A continuous flow reactor which can be heated was used as the etherification apparatus. For a given internal reactor diameter of 20 mm, the height of the catalyst bed was in each case chosen so that the reaction volume resulting therefrom, together with the amount of liquid employed, gave the desired throughput over the catalyst A. The reactor is equipped with several thermometers at intervals of in each case 100 mm in order to monitor the control temperature, it being possible for the temperature to be freely chosen in each case. The pressure of the reactor is regulated by a constant pressure device. The hydrocarbons are mixed with the alkanol in a mixing chamber upstream of the reactor. The molar ratio of active hydrocarbons to alkanol is 1:1. The materials fed into the reactor can be heated, if desired, and the part streams can be controlled by pumps. The reactor can be heated. The product leaving the reactor is intermediately stored in a cooled separator, before it is worked up in a subsequent distillation column. The tertiary alkyl alkyl ether can be removed as a side stream. The top product, which still contains active components, such as methylbutenes, can be recycled to the reactor inlet. The bottom product from the column contains higher ethers. The analyses are carried out by gas chromatography.

In a typical embodiment, the cation exchanger, as described in Example 1, is activated in a stream of hydrogen at 90° C. under 26 bars of $H_2$ for 48 hours, in the etherification apparatus. The reaction mixture is then metered in stepwise until a throughput over the catalyst A of 1 (ml/ml. hour) has been established. The etherification of active methylbutenes with methanol in an equimolar ratio to give tertiary amyl methyl ether (TAME) proceeds in the trickle phase at a reaction temperature of 110° C. and under a reaction pressure of 8 bars. After the throughput of the catalyst has remained constant for 60 hours, a sample of the mixture is taken in order to determine the end products by gas chromatography. The compositions of the feed material and end product are summarised in Table 1:

TABLE 1

|  |  | Starting material | End product |
|---|---|---|---|
| 2-methylbut-2-ene | (g) | 14.5 | 1.6 |
| 2-methylbut-1-ene | (g) | 3.8 | 0.2 |
| 3-methylbut-1-ene | (g) | 0.5 | <0.1 |
| methanol | (g) | 9.5 | 0.9 |
| TAME | (g) | — | 24.7 |
| Yield of TAME | (%) | — | 90.1 |

The remainder to make up to 100% by weight comprises higher compounds which are identified as ethers by IR spectroscopy, $C_5$- and $C_6$-olefins, higher olefins and paraffins.

EXAMPLE 3 (COMPARISON EXAMPLE)

A macroporous cation exchanger was prepared according to German Patent Specification No. 1,113,570, Example 3. The water-moist ion exchanger thus obtained was dried overnight by the conventional drying method at 90° to 100° C. and under 15 mm Hg in order to remove the water in the dry resin. The procedure of Example 2 was followed using the dry ion exchanger thus obtained, without carrying out partial charging with palladium and reduction thereof to the metallic state. The compositions of the feed material and end product can be seen from Table 2:

TABLE 2

| 110° C./8 bars |  | Starting material | End product |
|---|---|---|---|
| 2-Methylbut-2-ene | (g) | 14.5 | 3.4 |
| 2-Methylbut-1-ene | (g) | 3.8 | 2.2 |
| 3-Methylbut-1-ene | (g) | 0.5 | 0.4 |
| Methanol | (g) | 9.5 | 4.0 |
| TAME | (g) | — | 17.6 |
| Yield of TAME | (%) | — | 64 |

EXAMPLE 4

The experiments were carried out in the same manner as in Example 2, but using LEWATIT SPC 118 of Bayer AG containing 1.25 g of palladium/l of dried catalyst, after reduction with hydrogen. The results in Table 3 show the effect of pressure on the etherification:

TABLE 3

| 110° C./A = 1 |  | Feed material | End product 3 bars | 10 bars | 15 bars | 25 bars |
|---|---|---|---|---|---|---|
| 2-Methylbut-2-ene | (g) | 14.5 | 6.8 | 1.8 | 1.6 | 1.7 |
| 2-Methylbut-1-ene | (g) | 3.8 | 0.5 | 0.5 | 0.7 | 0.6 |
| 3-Methylbut-1-ene | (g) | 0.5 | 0.5 | <0.1 | 0.2 | 0.2 |
| Methanol | (g) | 9.5 | 5.4 | 1.1 | 1.2 | 1.2 |
| TAME | (g) | — | 16.1 | 24.1 | 23.9 | 23.8 |
| Yield of TAME | (%) | — | 58.5 | 87.8 | 87.2 | 86.7 |

Table 3 shows that, at 110° C. and with a throughput over the catalyst a of 1, the TAME yield is fairly constant under a pressure which ensures that a liquid phase is maintained and which is above about 8 bars at 110° C.

EXAMPLE 5

The experiments were carried out in the same manner as in Example 2, but using LEWATIT SPC 120 of Bayer AG with 2 g of palladium/l of dried catalyst, after reduction with hydrogen. The compositions of the feed material and end product given at the various reaction temperatures are summarized in Table 4:

TABLE 4

| 6 bars/A = 1 | | Feed material | End product | | | |
|---|---|---|---|---|---|---|
| | | | 70° | 90° | 100° | 110° |
| 2-Methylbut-2-ene | (g) | 14.5 | 3.2 | 2.0 | 1.6 | 1.6 |
| 2-Methylbut-1-ene | (g) | 3.8 | 1.7 | 0.5 | 0.4 | 0.3 |
| 3-Methylbut-1-ene | (g) | 0.5 | 0.3 | 0.1 | <0.1 | <0.1 |
| Methanol | (g) | 9.5 | 2.5 | 1.3 | 0.9 | 0.9 |
| TAME | (g) | — | 19.9 | 23.7 | 24.5 | 24.7 |
| Yield of TAME | (%) | — | 72.4 | 86.2 | 89.4 | 90.1 |

The results listed in Table 4 show that the best TAME yields were achieved at about 75° to 110° C.

EXAMPLE 6

The feed material was passed upwards through the catalyst bed at various throughputs over the catalyst a, samples being taken in each case after the throughput over the catalyst had remained constant for 24 hours. The catalysts decided in Example 2 are again used. The results for various throughputs over the catalyst are given in Table 5:

TABLE 5

| 80° C./10 bars | | Feed material | End product | | |
|---|---|---|---|---|---|
| | | | A = 0.5 | A = 1.0 | A = 1.5 |
| 2-Methylbut-2-ene | (g) | 14.5 | 1.2 | 2.3 | 2.6 |
| 2-Methylbut-1-ene | (g) | 3.8 | 0.2 | 0.3 | 0.6 |
| 3-Methylbut-1-ene | (g) | 0.5 | <0.1 | <0.1 | <0.1 |
| Methanol | (g) | 9.5 | 1.4 | 2.1 | 2.4 |
| TAME | (g) | — | 25.5 | 23.6 | 22.7 |
| Yield of TAME | (%) | — | 92.5 | 86.0 | 83 |

EXAMPLE 7

The experiments were carried out in the same manner and using the same catalyst as described in Example 2. However, the feed material was reacted with ethanol, instead of methanol, to give ethyl tertiary amyl ether.

TABLE 6

| 90° C./8 bars/A = 1 | | Feed material | End product |
|---|---|---|---|
| 2-Methylbut-2-ene | (g) | 15.7 | 1.5 |
| 2-Methylbut-1-ene | (g) | 2.6 | 0.3 |
| 3-Methylbut-1-ene | (g) | 0.5 | — |
| Ethanol | (g) | 13.1 | 1.1 |
| Ether | (g) | — | 30.1 |
| Yield of ether | (%) | — | 91 |

EXAMPLE 8

The experiments were carried out in the same manner and using the same catalyst as described in Example 2. A C4-hydrocarbon cut which also contains C4-olefins and paraffins, in addition to 44.1% by weight of isobutylene, was etherified, as the feed material, with methanol.

TABLE 7

| 12 bars/A = 1 | | Feed material | End product | |
|---|---|---|---|---|
| | | | 40° C. | 45° C. |
| Isobutylene | (g) | 44.1 | 1.3 | 1.2 |
| Methanol | (g) | 25.3 | 0.3 | 0.4 |
| Methyl tertiary butyl ether (MTBE) | (g) | — | 63.3 | 63.8 |
| Isobutylene conversion | (%) | — | 97.1 | 97.3 |
| MTBE yield | (%) | — | 91.3 | 92.0 |

EXAMPLE 9

The experiments were carried out in the same manner as in Example 2, but using the macroporous cation exchanger which had been prepared according to Example 1 and had been doped with the metals, reduced with hydrogen, given in Table 8.

TABLE 8

| 90°/8 bars | | Starting material | End product | | |
|---|---|---|---|---|---|
| | | | Chromium | Platinum | Iron |
| Exchanger doped with | | | 1.0 [g/l] | 1.0 [g/l] | 1.0 [g/l] |
| 2-Methylbut-2-ene | [g] | 14.5 | 2.0 | 1.5 | 4.8 |
| 2-Methylbut-1-ene | [g] | 3.8 | 0.6 | 0.2 | 1.2 |
| 3-Methylbut-1-ene | [g] | 0.5 | — | — | — |
| Methanol | [g] | 9.5 | 2.1 | 1.7 | 3.7 |
| TAME | [g] | — | 23.6 | 24.9 | 18.6 |
| Yield of TAME | [%] | — | 86.0 | 91.0 | 68.0 |

What is claimed is:

1. In a process for the preparation of an alkyl tert.-alkyl ether by reaction of an isoolefin branched at the double bond and an alkanol in the presence of a cation exchanger, the improvement which comprises:
   (a) employing as the cation exchanger a macroporous or gelatinous acid cation exchanger in the H+ form which has been charged with 0.1 to 5 grams, per one liter of dry cation exchanger, of an elementary form of a metal of sub-groups VI, VII or VIII of the periodic table of elements (Mendeleev) which cation exchanger is crosslinked with the degree of crosslinking of 2 to 65% and has a specific surface area of 5 to 750 square meters per gram on the basis of dry cation exchange resin; and
   (b) the reaction is carried out in the liquid phase at a temperature of 30° to 140° C. at a pressure of 2 to 100 bars employing a molar ratio of isoolefin to alkanol of 0.1 to 5.

2. A process according to claim 1, wherein the reaction is carried out in the presence of a solvent.

3. A process according to claim 1, wherein the metal of sub-groups VI, VII or VIII is selected from the group consisting of chromium, rhenium, palladium, platinum and, iron and mixtures thereof.

4. A process according to claim 1, wherein said cation exchanger is one prepared by depositing said metal of sub-groups VI, VII and VIII on said cation exchange resin in ionic form and thereon converting the same to elementary form by contact with hydrogen.

5. A process according to claim 4, wherein said metal is converted into the elementary form at 50° to 140° C. employing a hydrogen pressure of 2 to 50 bars.

6. A process according to claim 1, wherein the molar ratio of isoolefin to alkanol is 0.9 to 1.1.

7. A process according to claim 1, wherein the process is carried out at a space velocity of 0.1 to 10.

8. A process according to claim 1, wherein the reaction is carried out at a temperature of 50° to 130° C.

9. A process according to claim 1, wherein the process is carried out at a pressure of 3 to 30 bars.

10. A process according to claim 1, wherein the process is carried out employing a saturated, branched and/or unbranched hydrocarbon of at least 4 carbon atoms as solvent.

11. A process according to claim 1, wherein a recycle stream in a weight ratio of 0.1 to 10:1, relative to the feed stream, is additionally fed in for the etherification.

12. A process according to claim 1, wherein the process is carried out at a pressure of at least 5 bars.

13. A process according to claim 1, wherein the process is carried out at a pressure of at least 8 bars.

14. A process according to claim 1, wherein the process is carried out at a pressure of at least 10 bars.

* * * * *